United States Patent
Biernacki et al.

(10) Patent No.: US 7,680,304 B2
(45) Date of Patent: Mar. 16, 2010

(54) METHOD OF WOOD STRENGTH AND STIFFNESS PREDICTION

(75) Inventors: Jacek M. Biernacki, Salmon Arm (CA); Carl Flatman, Salmon Arm (CA); Ron Lahoda, Salmon Arm (CA); Steve Woods, Salmon Arm (CA)

(73) Assignee: Weyerhaeuser NR Company, Federal Way, WA (US)

( * ) Notice: Subject to any disclaimer, the term of this patent is extended or adjusted under 35 U.S.C. 154(b) by 922 days.

(21) Appl. No.: 10/854,930

(22) Filed: May 25, 2004

(65) Prior Publication Data

US 2005/0031158 A1 Feb. 10, 2005

Related U.S. Application Data

(60) Provisional application No. 60/473,385, filed on May 27, 2003.

(51) Int. Cl.
*G06K 9/00* (2006.01)
*G01B 11/02* (2006.01)

(52) U.S. Cl. .................. 382/108; 382/169; 702/170

(58) Field of Classification Search ............... 382/100, 382/108, 111, 123, 141, 149, 168, 184, 193, 382/195, 199, 203, 256, 274, 276, 315, 316, 382/305; 73/12.12, 597, 169; 324/663, 687; 702/179, 36, 29, 170
See application file for complete search history.

(56) References Cited

U.S. PATENT DOCUMENTS

| | | | |
|---|---|---|---|
| 4,500,835 A | | 2/1985 | Heikkila |
| 4,926,350 A | * | 5/1990 | Bechtel et al. ............... 702/36 |
| 4,941,357 A | | 7/1990 | Schajer |
| 5,394,097 A | * | 2/1995 | Bechtel et al. ............. 324/687 |
| 5,804,728 A | | 9/1998 | Beall et al. |
| 5,960,104 A | | 9/1999 | Conners et al. |
| 6,769,306 B2 | * | 8/2004 | Andrews et al. ............. 73/597 |
| 6,784,672 B2 | * | 8/2004 | Steele et al. ............... 324/663 |
| 6,813,927 B1 | * | 11/2004 | Harris et al. .............. 73/12.12 |
| 7,047,156 B1 | * | 5/2006 | Bechtel et al. ............ 702/179 |
| 2002/0025061 A1 | | 2/2002 | Metcalfe et al. |

FOREIGN PATENT DOCUMENTS

| EP | 0 403 020 A2 | 6/1990 |
|---|---|---|
| WO | WO 00/11467 A1 | 3/2000 |
| WO | WO 01/65253 A2 | 9/2001 |

* cited by examiner

*Primary Examiner*—Seyed Azarian
(74) *Attorney, Agent, or Firm*—Rachael Vaughn

(57) ABSTRACT

A method of non-destructive testing of a wood piece using a multiplicity of sensors. The method may include the steps of sensing the wood piece; collecting information from the sensors; and integrating the information into a physical model providing for strength and stiffness prediction. The collected information relate to material characteristics of the wood piece and to fiber quality characteristics of the wood piece. The material characteristics may include one or more of the following material characteristics of the wood piece: growth ring thickness; grain angle deviation; clear wood density; knot location; knot density; knot type; knot size; location in the tree from which the wood piece was cut. The fiber quality characteristics may include one or more of the following fiber quality characteristics: microfibril angle, juvenile wood, biodeterioration; reaction wood species; and manufacturing or drying defects including one or more of the following defects: sawcuts, checks, shake; size of actual cross-section, and species.

14 Claims, 15 Drawing Sheets

Figure 2a
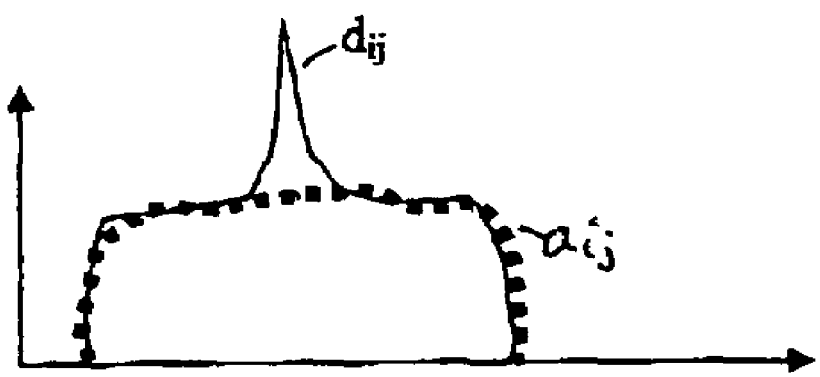
(a)
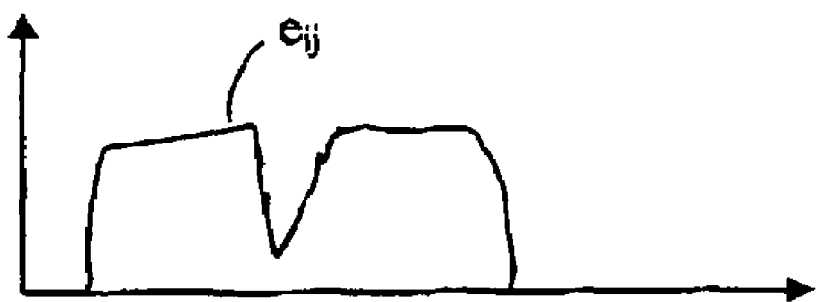
(b)
Figure 2b

METHOD OF WOOD STRENGTH AND STIFFNESS PREDICTION

CROSS REFERENCE TO RELATED APPLICATION

This application claims priority from U.S. Provisional Patent Application No. 60/473,385 filed May 27, 2003 entitled Method of Wood Strength and Stiffness Prediction.

FIELD OF THE INVENTION

The present invention relates generally to wood strength and stiffness prediction.

BACKGROUND OF THE INVENTION

It can be appreciated that wood strength grading has been in use for many years. This has traditionally been accomplished by using visual grading rules to predict strength. Other technologies such as mechanical bending and X-ray, to sense density, have been used to estimate the strength of wood.

The main problem with conventional visual wood grading is that is does not predict strength or stiffness accurately. The use of the mechanical bending improved the ability to predict stiffness of the lumber but the correlation to strength is poor. X-ray based systems predict strength and stiffness based on density only.

While these devices have been suitable for the particular purpose to which they addressed, they are not as suitable for highly accurate strength and stiffness prediction of today's variable and often low-quality wood resource.

SUMMARY OF THE INVENTION

The present invention provides a new prediction method of wood strength and stiffness.

The general purpose of the present invention, which will be described subsequently in greater detail, is to provide a new prediction method that has many of the advantages of the board strength prediction methods mentioned above and in addition, novel features that result in a greater prediction accuracy.

To attain this, the present invention includes generally the use of streams of sensor information integrating into a physical model providing for strength and stiffness prediction. It is to be understood however that the invention is not limited in its application to the details of the method and to any arrangements of the components set forth in the following description or illustrated in the drawings, or to the details of the algorithm employed. The invention is capable of other embodiments and of being practiced and carried out in various ways. Also, it is to be understood that the phraseology and terminology employed herein are for the purpose of the description and should not be regarded as limiting.

One object of the present invention is to provide a prediction of wood strength that will predict the strength and stiffness in the lumber based on a physical model using several sensing technologies. Physical model, in this context, refers generally to an algorithm that utilizes the material mechanical behavior and impact of various wood characteristics on strength and stiffness.

Another object is to provide a prediction of wood strength and stiffness that can integrate many technologies into a single model thereby providing differing accuracy prediction based on the sensors used.

Another object is to provide a prediction of wood strength and stiffness that with sensor technologies added together improves the ability of any one sensor to predict strength and stiffness.

To the accomplishment of the above and related objects, this invention may be embodied in the form illustrated in the accompanying drawings, attention being called to the fact, however, that the drawings are illustrative only, and that changes may be made in the specific construction illustrated.

In one aspect, the method of the present invention may be characterized as a method of, and corresponding computer program means for accomplishing, non-destructive testing of a wood piece using a multiplicity of sensors. The method may include the steps of, and the program the computer readable program code means for causing the controlling and processing of, the following:
  a) sensing the wood piece,
  b) collecting information from the sensors, and
  c) integrating the information into a physical model providing for strength and stiffness prediction.

The step of collecting information may include collecting information relating to material characteristics of the wood piece and relating to fiber quality characteristics of the wood piece. The material characteristics may include one or more of the following material characteristics of the wood piece: growth ring thickness; grain angle deviation; clear wood density; knot location; knot density; knot type; knot size; location in the tree from which the wood piece was cut. The fiber quality characteristics may include one or more of the following fiber quality characteristics: microfibril angle, juvenile wood, biodeterioration; reaction wood species; and manufacturing or drying defects including one or more of the following defects: sawcuts, checks, shake; size of actual cross-section, and species.

In one embodiment the method further includes the steps of providing one or more of the following sensor types: X-ray, microwave, camera vision, laser triangulation three-dimensional geometry, material vibration measurements, laser based tracheid effect measurement.

The method and software (alternatively referred to as a computer program product) for implementing same may also be characterized as including, respectively, the following steps or program code means for causing the implementation of the following steps:
  a) Measuring of the piece with a multiplicity of sensors;
  b) Estimating wood volume characteristics, including one or more of the following: clear wood density, grain angle, moisture content, growth ring angle, location in the tree from which the wood was cut, fiber quality including mirofibril angle, and three dimensional geometry of a scanned object;
  c) Detecting size, location and classification of wood defects, including one or more of the following: knots, biodeterioration, reaction wood, juvenile wood, manufacturing and drying defects, pith, pitch, wet pockets;
  d) Subsequently inputting corresponding measured, estimated or detected information from the measuring, estimating or detecting steps into a physical model of the wood piece;
  e) Predicting strength and stiffness based on the effect of the estimated information from the step of estimating the volume characteristics and the detected information from the step of detecting size, location and classification of wood defects on mechanical behavior of the wood piece.

The further step of constructing clear wood density equivalent as a first step in strength and stiffness prediction may also include; comprising:
  a) Measuring of material density in a plurality of dimensions, for example using x-ray sensors, b) Estimating other wood volume characteristics, including grain angle, growth ring angle, location in the tree from which the wood piece was cut, fiber quality including microfibril angle, and 3D geometry of the scanned piece, c) Reducing clear wood equivalent density by the effect of the wood volume characteristics using relationships of these characteristics on mechanical behavior of wood.

d) Detecting size, location and classification of wood defects, including but not limited to, knots, biodeterioration, reaction wood, juvenile wood, manufacturing and drying defects, pith, pitch, wet pockets, e) Further reducing clear wood equivalent density by the effect of wood defects in respective locations of occurrence and effect these characteristics on mechanical behavior of wood;

f) Constructing strength and stiffness models using clear wood density equivalent.

The further step of constructing clear zero grain angle wood equivalent as a first step in strength and stiffness prediction may also be included, comprising:

a) Measuring of material grain angle in a plurality of dimensions, b) Constructing clear wood zero grain angle equivalent by assigning a nominal density value which is an average for a wood species whenever grain angle relative to a longitudinal axis of the piece is zero, and less wherever the grain angle deviates from zero and accordingly to grain angle effect on mechanical behavior of the wood piece, c) Reducing clear wood equivalent density by the effect of the wood volume characteristics using theoretical and empirical relationships of these characteristics on mechanical behavior of wood, d) Further reducing clear wood equivalent density by the effect of wood defects in their respective locations of occurrence and the effect on mechanical behavior of the wood piece, and e) Constructing strength and stiffness models using clear wood density equivalent.

The further step may be included of estimating clear wood equivalent in an area of the wood piece occupied by a knot by virtually removing density occupied by a knot and replacing it by a density of clear wood, mechanically equivalent to the removed knot.

The sensors may include a sensor collecting pixel values from a corresponding matrix of pixels in the sensor, and wherein for every pixel density, $d_{ij}$, the method and software includes the step of computing clear wood equivalent, $e_{ij}$, using adaptive threshold clear wood density, $a_{ij}$, in the equation:

$$e_{ij} = \text{RemaingClearWood} + \text{KnotEquivalent}$$

wherein:

$$\text{RemaingClearWood} = a_{ij} - k_{ij}*K$$

i is virtual pixel index along the length of the wood piece
j is virtual pixel index traversely across the wood piece
K is knot density ratio, defined as a ratio of clear wood density to density of knot
knot density is difference between wood density $d_{ij}$ and clear wood density $$k_{ij} = d_{ij} - a_{ij}$$

KnotEquivalent is defined as clear wood density equivalent residing in knot volume, $$\text{KnotEquivalent} = k_{ij}*K*M$$

wherein M is the material knot property ratio:

$$M = \text{Knot Property/Clear Wood Property}.$$

The step of computing $e_{ij}$ may include substituting:

$$e_{ij} = a_{ij} + (d_{ij} - a_{ij})*K*(M-1).$$

The step of predicting strength and stiffness may include the step of estimating effect of the grain angle by decomposing the grain angle into running average and local deviation components, wherein the running average component is a function ($g_{ave}$ (GA)) of running average grain angle along a length of the wood piece excluding grain deviations around knots, and wherein the local deviation component is a function ($g_{dev}$ (GA)) of the grain angle defined as a difference between a local measured grain angle and the running average grain angle. The method and software further includes the step of computing grain angle effect functions $g_{ave}$ (GA) and $g_{dev}$ (GA) for determining the effect of grain angle on a material property wherein both $g_{ave}$ (GA) and $g_{dev}$ (GA) are computed according to the following equation:

$$g(GA) = \frac{1}{R \cdot \sin^n(GA) + \cos^m(GA)}$$

n and m are empirical constants, R is the ratio between the material property measured parallel to the grain versus the material property measured perpendicular to the grain. Optimizing constants R, n, and m are specific to the wood species corresponding to the wood piece.

a) The method and software further include the steps of:
applying the running average modification function ($g_{avg}$ (GA)) to the clear wood equivalent density by multiplication according to:

$$e'_{ij} = e_{ij}*g_{avg}(GA_{ij})$$

b) modifying the grain deviation function ($g_{dev}$(GA)) to derive a further grain angle deviation modification function to avoid multiple density reduction due to knot detected in density according to:

$$g'_{dev}(GA_{ij}, k_{ij}) = g_{dev}(GA_{ij}) + (1 - g_{dev}(GA_{ij}))k_{ij}/T$$

wherein T is a constant threshold value density, and c) applying the grain angle deviation modification function $g'_{dev}(GA_{ij}, K_{ij})$ to clear wood equivalent density by multiplication $$e'_{ij} = e_{ij}*g'_{dev}(GA_{ij}, k_{ij}).$$

The method and software may further include the step of estimating a moisture content effect function, m(MC), in the clear wood density equivalent by computing m(MC) with a reference to 12% moisture content wherein $$m(MC) = \text{either } A - B*MC \text{ for } MC < MC_{sat}, \text{ or}$$

$$m(MC) = m_{sat} \text{ for } MC \geq MC_{sat}$$

Where $$B = (P-1)/(0.12 - MC_{sat} - 0.12*P)$$

$$A = 1 + 0.12*B$$

$$M_{sat} = A - B*MC_{sat}$$

P is the ratio of a material property of interest when the wood piece is saturated with moisture to the same material property when the wood piece is oven-dry
$P = S_{sat}/S_o$
$MC_{sat}$ is fiber saturation point moisture content within the percentage range 25 to 30%.

The method and software may further include the step of estimating a modulus of elasticity (MOE) profile of a section of the wood piece using estimation of modulus inertia computed from a clear wood density equivalent by:

(a) computing an inertia profile along a longitudinal axis of the wood piece according to:

$$I_i = \Delta x^3 \sum_{j=1}^{K} (c_i - j)^2 \cdot e_{ij}$$

wherein the longitudinal axis is in an x-axis direction, and wherein $\Delta x$ is a pixel increment in the x-axis direction, and wherein center of gravity is computed according to:

$$c_i = \frac{\sum e_{ij} \cdot j}{\sum e_{ij}}$$

and wherein $e_{ij}$ is clear wood equivalent density;

(b) computing MOE within a longitudinal window on the wood piece, wherein $MOE_k = f(I_i, k)$, and wherein $f(I_i, k)$ is a function that estimates the MOE in location k, using the inertia profile $I_i$, whereby $MOE_k$ provides an estimate of the MOE along the board main axis, to provide an MOE profile. The function $f(I_i, k)$ may be estimated using weights $W_j$ according to:

$$f(I_i, k) = \sum_{j=1}^{M} W_j \cdot I_{k+i-M/2}$$

The function $f(I_i, k)$ may also be calculated as a close-form solution modulus of inertia profile according to:

$$E_{Est} = D \frac{1}{K}$$

wherein $$K = \Delta x^2 \left( \sum_{N/2} \sum_{N/2} y_i - \frac{1}{2} \sum_{N} \sum_{N} y_i \right)$$

$\Delta x$ is a discrete increment in the direction of the x axis, $$y_i = \frac{w_i}{J_i}$$

$w_i$ is discrete representation of $w(x)$, and
$J_i$ is $I_i$

The step of estimating modulus of elasticity from the MOE profile may use a low point or an average of the MOE profile.

The method and software may include the step of constructing clear wood density equivalent of a limited section of the wood piece, wherein the limited section is translated along the grain direction axis of the wood piece. The step of constructing clear wood density equivalent may include:

(a) computing minimum clear wood equivalent density profile in a window of the wood piece and running the window along the grain direction axis of the wood piece such that the window combines adjacent weak areas $$e_j^{MIN} = \text{Min}_{i=0}^{i=W-1} (e_{ij})$$

wherein i is pixel index within window, i=0 ... W-1, along the grain direction axis, wherein the grain direction axis is in the nominal grain direction of the wood piece
j is index perpendicular to the grain direction axis, (b) computing weighted clear wood equivalent density for the entire section $$e = \sum_{j=1}^{N} w_j \cdot e_j^{MIN}$$

wherein $w_j$ is a cross-sectional weight which is greater at edges of the wood piece and reduced in the middle of the wood piece between the edges, (c) computing tension strength (UTS) and bending strength (MOR) from e $$UTS = f^{UTS}(e)$$

$$MOR = f^{MOR}(e)$$

Where $f^{UTS}$ and $f^{MOR}$ are empirical relationships between clear wood density and strength.

The strength functions $f^{UTS}$ and $f^{MOR}$ may be determined according to $$UTS = f^{UTS}(e) = Ae^p$$

and $$MOR = f^{MOR}(e) = Be^r$$

wherein A, p, B, r are empirical constants.

The method and software may also include the further step of estimating bending and tension strength of at least a portion of the length of the wood piece by determining a minimum of a lengthwise strength profile of the wood piece.

The method and software may further include the step of refining the model by optimization of model parameters to minimize prediction error. For example, the model may be optimized for a particular wood species for particular commercial dimension lumber size.

In the method and software the step of collecting information relating to fiber quality may include the step of estimating fiber quality by measuring a vibration frequency of the wood piece, wherein the vibration frequency is a result of vibration induced only by feeding of the wood piece in an infeed feeding the wood piece, for example between a plurality of infeed rolls, to the sensors and without any explicit means vibration-inducing impact means.

The method and software may further include the step of estimating bending and tension strength of the wood piece by measuring a vibration frequency of the wood piece wherein the vibration frequency is a result of vibration induced only by feeding of the wood piece in an infeed feeding the wood piece to the sensors and without any explicit vibration-inducing impact means.

At least two pairs of infeed rolls and two pairs of outfeed rolls, respectively upstream and downstream of the sensors, may be employed. A non-contact optical scanner may be employed to measure the vibration frequency, which may be measured by dividing the vibration signal into different sections corresponding to the support and constraint conditions of the wood piece on the infeed or the outfeed rolls. The support conditions may be unconstrained, semi-constrained, or fully-constrained.

In the method a parameter E may be calculated according to:

$$E = Kf2m/I$$

wherein E is estimated MOE, K is a constant than contains the effect of the type of constraint, whether unconstrained, semi-constrained or fully constrained, as well as board span effect, I is a constant for a particular board cross-sectional size and m is distributed mass. m may be assumed constant, or measured, for example by a scanner using a radiation source.

In the method and software, the moisture content may be estimated using microwave measurement, or using microwave measurement and density estimation, and density characteristics may be measured by a scanner using a radiation source. The moisture content (mc) may be computed according to:

$$mc = Ka^n$$

where K and n are empirical constants, and a is microwave amplitude. The microwave amplitude may be measured when an applied microwave radiation is polarized in a direction transverse to a longitudinal axis of the wood piece. The moisture content (mc) may also be computed according to:

$$mc = Ka^n d^m$$

where K, m, and n are empirical constants, a is microwave amplitude, and d is density, which may be measured by a scanner using a radiation source. Moisture content and microwave amplitude may be corrected for temperature.

The lumber value of the lumber may be maximized by cutting lumber or end trimming lumber based on estimated modulus of elasticity profile, wherein increased lumber value of the lumber is achieved by trimming off a part of the lumber board having a grade reducing property.

The computer program product according to one aspect of the present invention includes computer readable program code means for causing refining the physical prediction model of the workpiece by computer readable program code means for causing optimization of model parameters to minimize prediction error. Input variables in the property (strength or stiffness) physical prediction model include collected board data and model parameters. The Predicted Property=f (Model Parameters, Board Data), where, Model Parameters= $(p_1, p_2, p_3, \ldots, p_N)$ and Board Data is the sensor information gathered about the wood piece as set out above. The error to be optimized is a measure of the difference between predicted property and observed property, for example absolute value of the difference, that is Error=AbsoluteValue (Predicted Property−Observed Property). The optimization of model parameters is achieved by minimizing combined error of a large sample of boards. For example, combined error for a sample of boards is a sum of the errors, as defined above, that is SumOfErrors=Sum($Error_i$). Combined error could be quantified in various ways, including R-square, root-mean-squared error, etc. Optimization is implemented by varying values of Model Parameters so the combined measure of the error for a sample in minimized. Various optimization algorithms may be employed, for example genetic algorithm, random walk, direction set (Powell's) method, etc as would be known to one skilled in the art.

BRIEF DESCRIPTION OF THE DRAWINGS

In the accompanying drawings, in which like reference characters designate the same or similar parts throughout the several views:

FIG. 2A illustrates steps involved in clear wood density computing for a density cross-section showing original density $d_{ij}$ and adaptive threshold $a_{ij}$.

FIG. 2B illustrates steps involved in clear wood density computing for a density cross-section, showing clear wood equivalent density $e_{ij}$.

FIG. 5 illustrates board behavior as the board passes through the linear grading machine. Characteristic points A, B, C, and D define different sections in the linear profile sensor profile corresponding to different support conditions of the board, wherein:

a) in FIG. 5A the board leading end is at point A
b) in FIG. 5B the board leading end is at point B
c) in FIG. 5C the board leading end is at point C
d) in FIG. 5D the board leading end is at point D

DETAILED DESCRIPTION OF EMBODIMENTS OF THE INVENTION

Figure 1:
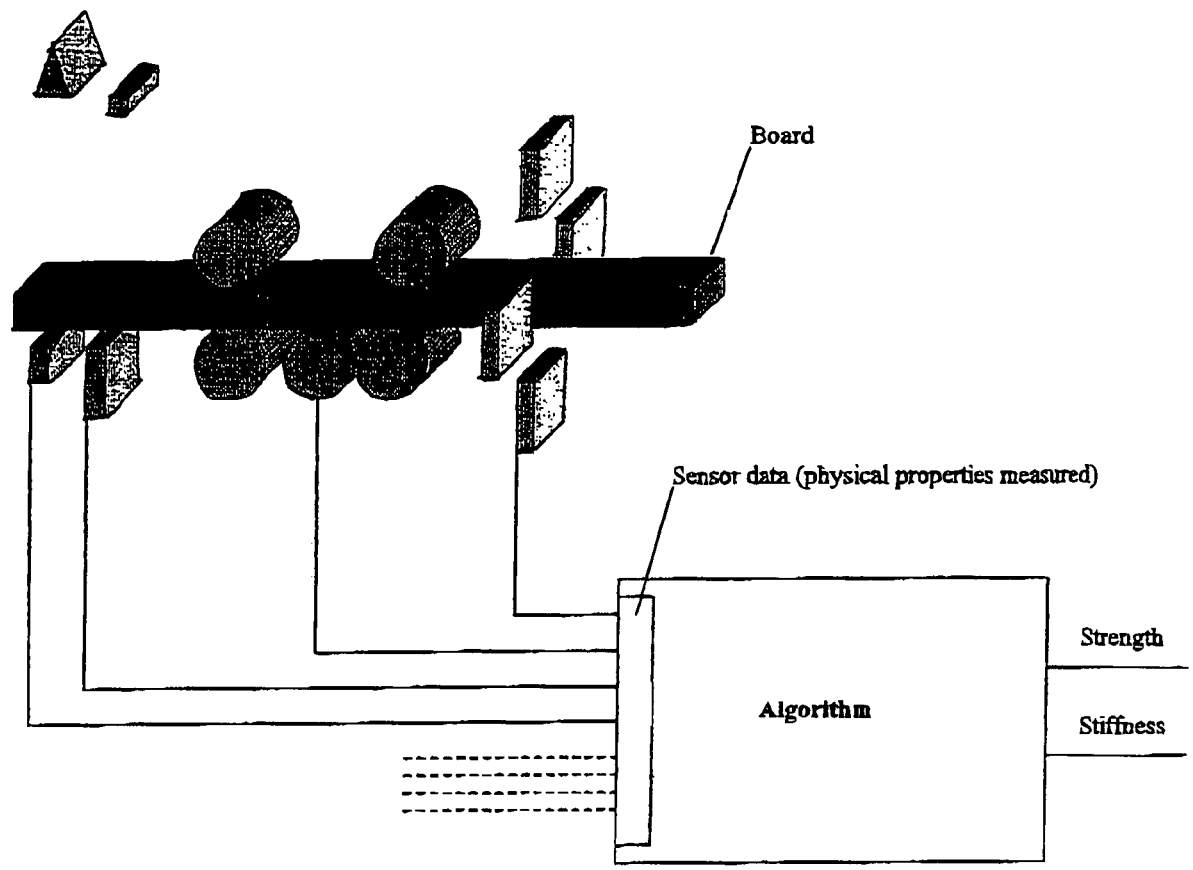
FIG. 1 is a diagrammatic view of multiple sensors measuring attributes and properties of a board for physical modeling by a processor algorithm to predict strength and stiffness of the board as algorithm outputs.

We have developed a machine to predict the strength and stiffness of wood based on a physical model using several sensing technologies. A physical model is an algorithm that relates the sensor information to the strength/stiffness of the material based on physical properties of the material and other characteristics, such as defects. The machine can integrate many sensing technologies into a single model and provides differing accuracy prediction based on the types and number of sensors used. In one embodiment, this technology builds on an X-ray based strength-grading machine, such as sold by Coe Newnes/McGehee ULC under the trademark XLG (X-ray Lumber Gauge).

The following physical aspects of wood effect strength and stiffness of wood directly: wane, moisture content, Modulus of Elasticity including whether measured flatwise or edgewise, growth ring thickness or density (rings/inch), grain angle deviation, density, knots (location, density, type and size), location in the tree from which the wood was cut, fiber quality, such as mirofibril angle, juvenile wood, biodeterioration, etc., reaction wood species, manufacturing and drying defects, such as sawcuts, checks, shake, etc. and, size of actual cross-section.

These wood aspects are measured or predicted with various sensing technologies and the data is used to predict the wood strength and stiffness. The reason to choose a physical model over other techniques such as a neural network, regression, or functional approximation model, is the stability and low training requirements. The model is based on the physical characteristics of the wood and how they affect the strength and stiffness directly rather than a statistical model. The sensor technologies added together improve the ability of any one sensor to predict strength and stiffness.

The object is to have the predicted wood characteristics match the observed characteristics. The sensor technologies that can be used include but are not limited to the following: density map, moisture content, slope of grain map, growth ring measurements, dynamic wood bending for stiffness measurement, dynamic oscillation to determine stiffness, wood fiber quality determination (color vision, gray scale, infrared, etc), determination of species, profile measurement, location wood is cut from in the tree, and mechanical wane propagation measurement.

Combining some or all of these physical measurements, for example as combined according to the detailed methodology described below, leads to a better-predicted wood strength and stiffness accuracy.

With respect to the following description then, it is to be realized that the optimum relationship between the components and steps of the invention, to include variations in method, components, materials, shape, form, function and manner of operation, assembly and use, are deemed readily apparent and obvious to one skilled in the art, and all equivalent relationships to those illustrated in the drawings and described in the specification are intended to be encompassed by the present invention.

Clear Wood Equivalent

Clear wood equivalent (CWE) is used as an input to specific strength and stiffness models. Various prediction models may be used or developed based on this concept, such as prediction of ultimate tensile strength, modulus of rupture, etc. The CWE method approximates equivalent properties of a section of material in terms of density.

Figure 1A:
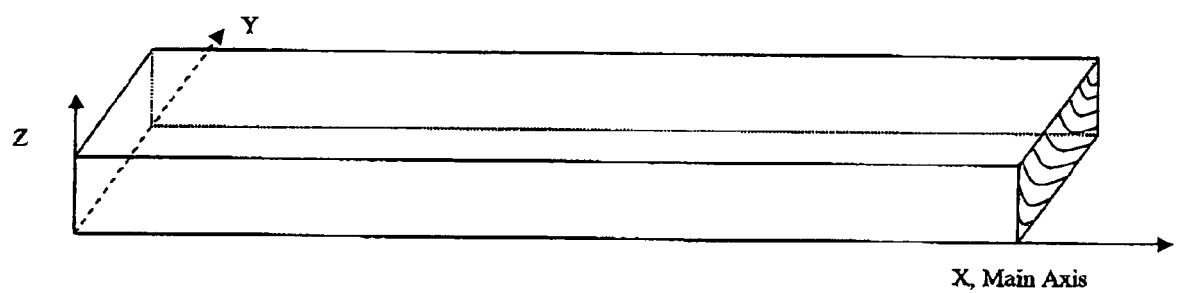
FIG. 1A illustrates board coordinates, showing the main axis (X) along the nominal grain angle direction.
Figure 1B:
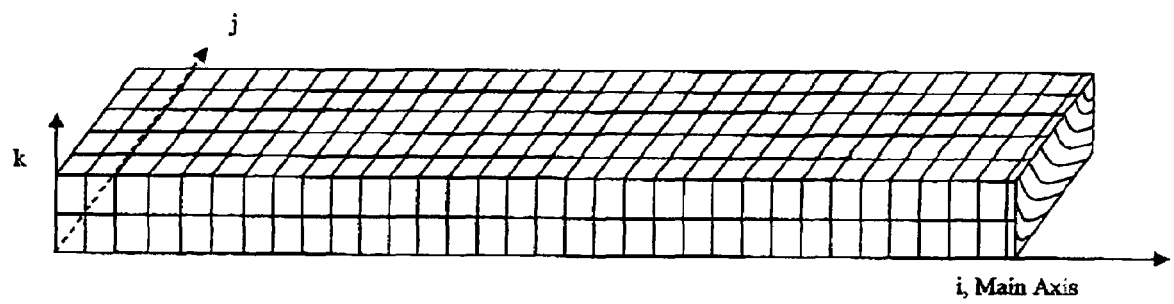
FIG. 1B illustrates a board divided into a 3-dimensional grid of discrete elements, showing index notation for different directions.

Wood, in a coordinate system such as seen in FIG. 1A, is divided into a grid of virtual pixels (rectangular section) in the face plane or 3-dimensionally, as illustrated in FIG. 1B. The size of the virtual pixels is configurable so as to be optimized. Initially a reference density from calibrated X-ray measurement is assigned to a pixel. Reference density is taken from density adaptive threshold. Following this, the initial density is modified by various wood characteristics, among which the most important is knot modification. The resulting density is equivalent to clear wood. In this context clear wood is defined as straight grained, defect-free, with a reference moisture content of 12%. FIG. 1D shows an example of an actual density profile (ADP) along with its corresponding reference density profile (RDP) and corresponding clear wood equivalent (CWE) density profile along the main axis X. The equivalent to clear wood is then used directly for strength and stiffness using various algorithms, known relationships, etc.

Some of the following steps may be in used in clear wood equivalent density approximating of a virtual pixel:

a) Start with reference density (adaptive threshold) at a virtual pixel.

b) modify initial density for knots by considering presence of a knot in a location if the difference between the reference and actual density of the knot is non-zero.

c) segment into regions so that a region contains a knot, use the segmented regions to recognize the knots region or regions.

Different modification functions are used for the following knot types: sound through knot, sound edge knot, sound intermediate knot, loose through knot, loose edge knot, loose intermediate knot.

Knot modification uses a concept of replacing a knot by its equivalent in terms of fiber strength or stiffness. This involves virtually removing the knot, computing remaining clear fiber volume, computing volume of the removed knot and adding the strength/stiffness equivalent of the knot to clear fibers. For every pixel density, $d_{ij}$, clear wood equivalent, $e_{ij}$, is computed using adaptive threshold $a_{ij}$ (see FIGS. 2a and 2b)

$$e = \text{RemainClearWood} + \text{KnotEquivalent} \quad (1)$$

Where, $$\text{RemainClearWood} = a_{ij} - k_{ij} * K \quad (2)$$

i is virtual pixel index along wood length (virtual line index)

j is virtual pixel index across wood length (virtual detector index)

K is knot density ratio, defined as a ratio of Clear Wood Density to Knot Density and knot density is $$k_{ij} = d_{ij} - a_{ij} \quad (3)$$

KnotEquivalent is defined as clear wood density equivalent residing in knot volume, $$\text{KnotEquivalent} = k_{ij} * K * M \quad (4)$$

Where M is property (stiffness or strength) knot ratio $$M = \text{Knot Property/Clear Wood Property} \quad (5)$$

The above relationships may be simplified to $$e_{ij} = a_{ij} + k_{ij}*K*(M-1) \quad (6)$$

or $$e_{ij} = a_{ij} + (d_{ij} - a_{ij})*K*(M-1) \quad (7)$$

Grain Angle Modification

Grain angle is measured or estimated using one or more of the following techniques: microwave, optical, tracheid effect on face plane, 2D angle, tracheid effect on face plane and edges, 3D angle, growth ring pattern analysis with vision images (color or gray-scaled images), tracheid effect and growth ring pattern analysis with vision images. This algorithm accounts for the presence of a knot and grain deviation in the same location. Grain angle is decomposed into two components: local average, and, local deviation.

Grain angle (GA) effect function for both average and the deviation, g(GA), reflects the relationship of grain angle vs. strength (or stiffness). This is derived from Hankinson's formula (Bodic 1982), $$g(GA) = \frac{1}{R \cdot \sin^n(GA) + \cos^m(GA)} \quad (8)$$

where n, m, are empirical constants, initially n=m=2, (optimized).

R is the ratio between the property of interest (strength or stiffness) parallel to perpendicular to the grain.

Constants R, n, and m are to be optimized, with a restriction that the g(GA=0)=1 and $1 \geq g(GA) > 0$ for any GA. Modification function g(GA) is applied to CWE density by multiplication of $$e'_{ij} = e_{ij}*g(GA_{ij}) \quad (9)$$

In case of grain deviation, g(GA) is further modified to account for a knot in the same location to eliminate a multiple CWE density reduction $$g_{dev}(GA_{ij}, k_{ij}) = g(GA_{ij}) + (1 - g(GA_{ij}))k_{ij}/T \quad (10)$$

Where, T is a threshold value in terms of density.

Important to the property of this relationship is if $k_{ij}=T$, then grain deviation modification has no effect:

$$g_{dev}(GA_{ij}, k_{ij}=T) = 1 \quad (11)$$

Both local average and local deviation are applied independently to CWE density.

Moisture Content Modification

The moisture content effect function, m(MC), reflects the known effect of moisture content on strength or stiffness. This relationship is modeled as a linear (downward) for MC<$MC_{sat}$=~25%, and constant, m(MC)=$m_{sat}$, for MC>=$MC_{sat}$. Ratio m($MC_{sat}$)/m(0) corresponds to the ratio between a property (MOE, MOR, UTS) at saturation to oven dry, P=$S_{sat}/S_o$. Based on literature, this ration is about 0.5 for UTS and MOR and 0.7 for MOE. Since the basis for our computations is property at MC=12% then m(12%)=1.0.

Therefore the requirements for the m(MC) are:

a. MC effect function is linear with a negative slope in the MC range from zero to saturation, and constant afterwards, $$m(MC) = \begin{cases} A - B*MC & \text{for } MC < MC_{sat} \\ m_{sat} & \text{for } MC \geq MC_{sat} \end{cases} \quad (12)$$

b. Property ratio $$P = \frac{S_{Sat}}{S_O} = \frac{m(0)}{m_{Sat}} \quad (13)$$

Initially, $$P = 0.5 \text{ for MOR and UTS (strength)} \quad (14)$$

$$P = 0.7 \text{ for MOE (stiffness)}$$

c. MC effect function is unity at nominal moisture content of 12%

$$m(12\%) = 1.0 \quad (14a)$$

Solution for m(MC), Linear Model
Solving equations (12) to (15), gives $$B = (P-1)/(0.12 - MC_{sat} - 0.12*P) \quad (15)$$

and $$A = 1 + 0.12*B \quad (15a)$$

For example, for P=0.5 and $MC_{sat}$=0.25,
A=1.3158
B=2.632
m($MC_{sat}$)=0.6579

Figure 3:
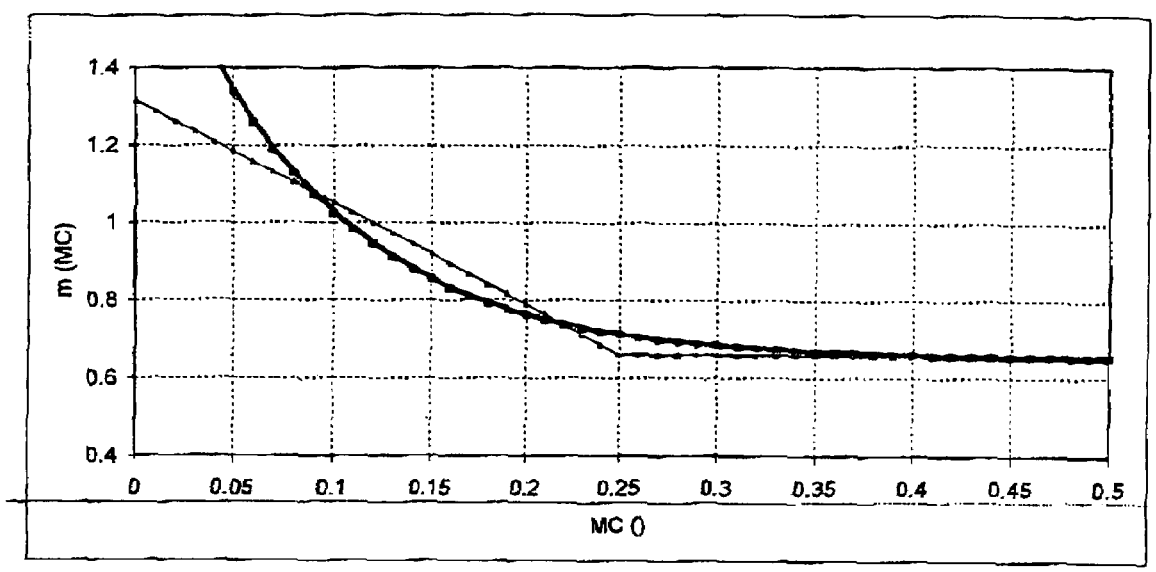
FIG. 3 are linear and nonlinear models of a function reflecting effect of moisture content m(MC).
Figure 3A:
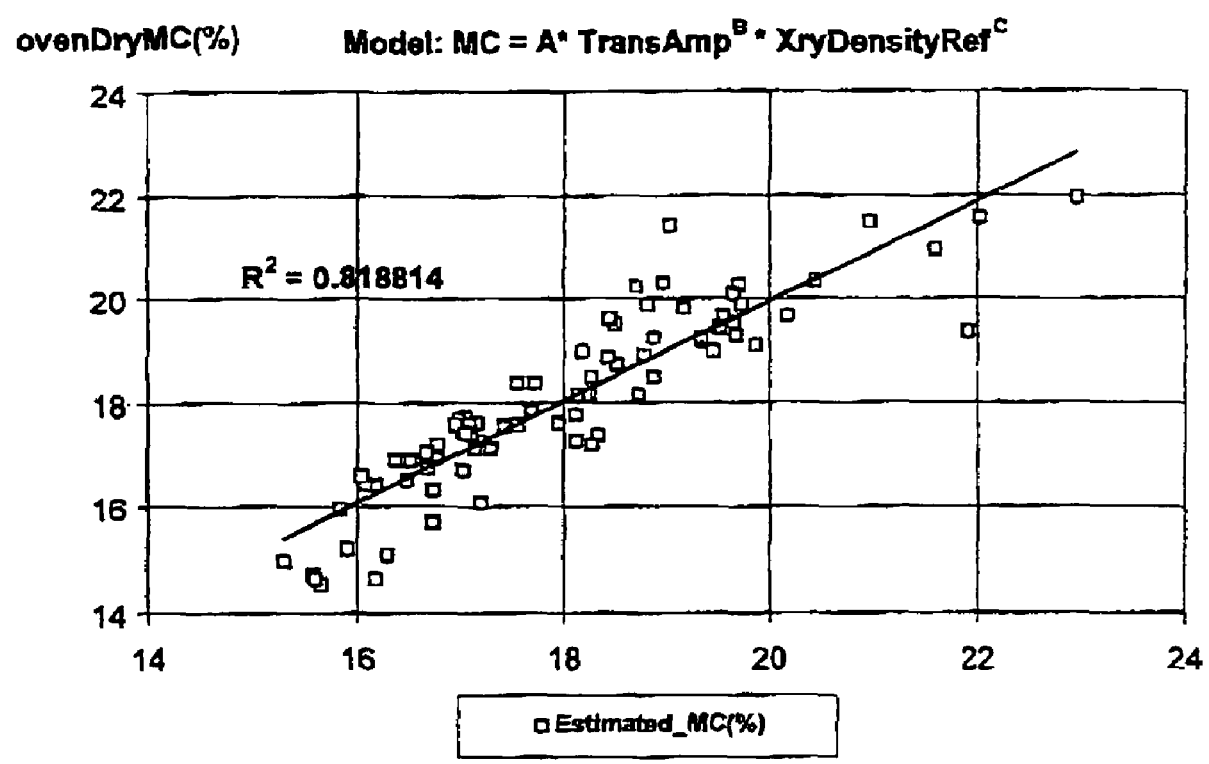
FIG. 3A is a moisture content prediction model showing predicted vs. oven-dry moisture content for southern yellow pine (SYP).

FIG. 3 shows the linear model using the above constants and two nonlinear models:

$$m(MC) = 0.65 + 0.3 * e^{-12*MC} \quad (16)$$

$$m(MC) = 0.65 + 9.29^{-5.45*MC} \quad (17)$$

Pith Modification $$e'_{ij} = e_{ij}*p(\text{amount of pith present}) \quad (18)$$

Where p( ) represents effect of pith on strength and stiffness.

Growth Ring Thickness Modification. Predicted Based on X-ray and Vision $$e'_{ij} = e_{ij}*g(\text{growth ring thickness}) \quad (19)$$

Where g ( ) represents effect of growth ring thickness on strength and thickness.

Place within Tree Modification.

Place within tree quality parameter is predicted based various scanning technologies $$e'_{ij} = e_{ij}*t(\text{place within tree modification quality parameter}) \quad (20)$$

Where t( ) is a function representing effect of position within tree.

Other Wood Characteristics Modification, Rot, Wane, Check, Resin Content, Compression Wood, Etc.

This set of modifications follow similarly to the modification analogues set out above for grain angle, moisture content, etc.

3D Clear Wood Equivalent

This approach expands the two-dimensional CWE model as described above to three-dimensions (3D). Virtual pixels are defined in 3D. Knots, checks, and other defect modifications are done based on 3D-defect detection. Other multiple sided defects such as checks are also included. This includes two approaches:

a) Density collected in 2D, knots, checks modifications entered as 3D, resulting with 3D grid of clear wood equivalent density b) Density collected in 3D with a CT scanner, knots, checks, and other 3D-defect modifications entered as 3D objects, resulting with 3D grid of clear wood equivalent density.

Clear Wood Equivalent Based on Grain Angle

This approach follows the one of CWE density described to this point, but the density is replaced with grain angle. First a grain angle is assigned to a grid element. Then the GA is modified by density, knots, moisture content, and other defects. Grain angle CWE is then used in actual models to predict strength and stiffness. This refers primary to lumber grading, but is not limited to this type of products.

Stiffness Prediction Using Moment of Inertia

Stiffness (Modulus of Elasticity) is predicted based on approximated cross sectional moment of inertia $J_i$ computed from clear wood equivalent model.

In general, moment of inertia I is defined in x direction for any cross-section with an area A (Popov 1968)

$$I = \int_A (c-x)^2 dA \tag{21}$$

Where c is center of gravity of the cross-section A.

In our case, I is approximated by $J_i$ in terms of density, reflecting both geometry of the cross-section as well as local stiffness $$J_i = \Delta x^3 \sum_{j=1}^{N} (c_i - j)^2 \cdot e_{ij} \tag{22}$$

Where $\Delta x$ represents pixel increment in x-axis direction and center of gravity is given as $$c_i = \frac{\sum e_{ij} \cdot j}{\sum e_{ij}} \tag{23}$$

To increase processing speed, $c_i$ does not have to be computed for every cross-section, but assumed to be equal to nominal center of the cross-section.

Two different approaches are given here to compute MOE from the $J_i$ profile. In both cases MOE is computed on a section of $J_i$ profile. The section is then moved along the board main axis X and MOE computed for another section of the board, as illustrated in FIG. 1F. This procedure yields a MOE profile along the main axis X.

First, a simple solution is given where MOE is simply weighted average of the $J_i$ $$MOE = \sum_{i=1}^{M} W_j \cdot J_j \tag{24}$$

Where $W_j$ is optimized windowing (sectioning) function.

Although, the equation (24) provides a simply and fast way of MOE prediction, a more sound but slower approach is to derive MOE directly from moment of inertia I. Following derivation follows well-known theory of mechanical behavior of solids (Popov 1968).

Moment of inertia is assumed to be a variable quantity within a span s, as shown in FIG. 1F. For a board section loaded with force F, as in FIG. 1G, equations for moments are $$w(x) = \frac{x}{2} \quad \text{for } 0 < x \leq s/3 \tag{24b}$$

$$w(x) = \frac{s}{6} \quad \text{for } s/3 < x \leq s2/3 \tag{24c}$$

$$w(x) = \frac{1}{2}(s-x) \quad \text{for } s2/3 < x \leq s \tag{24d}$$

The basic equation for beam deflection is $$\frac{M(x)}{E(x)I(x)} = \frac{dV^2(x)}{dx^2} \tag{24e}$$

Where E(x) represent MOE in location x,

I(x) moment of inertia profile,

V(x) deflection profile.

A further simplification combines E and I into one quantity J(x), which reflect a local stiffness of the cross-section.

$$J(x) = E(x)I(x) \tag{24f}$$

The equation (24e) simplifies into $$\frac{M(x)}{J(x)} = \frac{dV^2(x)}{dx^2} \tag{24g}$$

Following, the equation (24g) is solved for deflection $V_{max}$ at x=s/2 using direct integration method, applying boundary conditions, and converting to discrete format gives $$K = \frac{V_{max}}{F} = \Delta x^2 \left( \sum_{N/2} \sum_{N/2} y_i - \frac{1}{2} \sum_N \sum_N y_i \right) \tag{24h}$$

Where $\Delta x$ in a discrete increment in direction of the X axis, $$y_i = \frac{w_i}{J_i} \tag{24i}$$

$w_i$ is discrete representation of w(x), $J_i$ is discrete representation of J(x), the moment of inertia estimation computed from clear wood equivalent density.

Figure 1C:
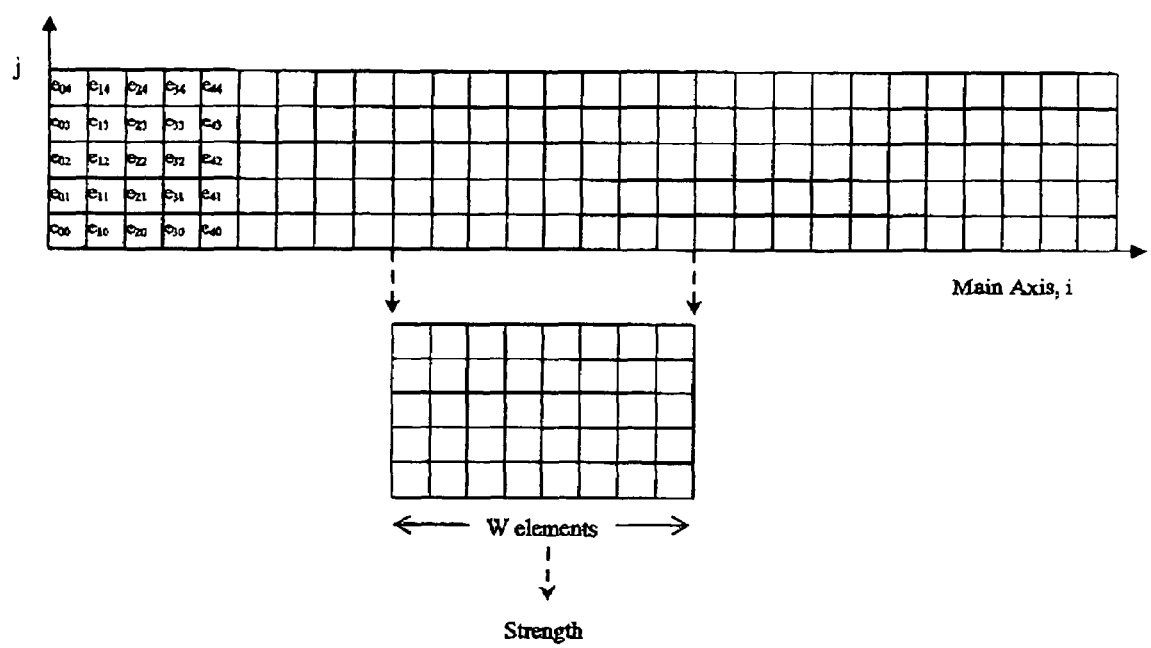
FIG. 1C illustrates a board divided into a 2-dimensional grid of discrete elements, showing notation of clear wood equivalent elements $e_{ij}$ and a section of length W taken from it to estimate strength assigned a location in the center of the section.
Figure 1D:
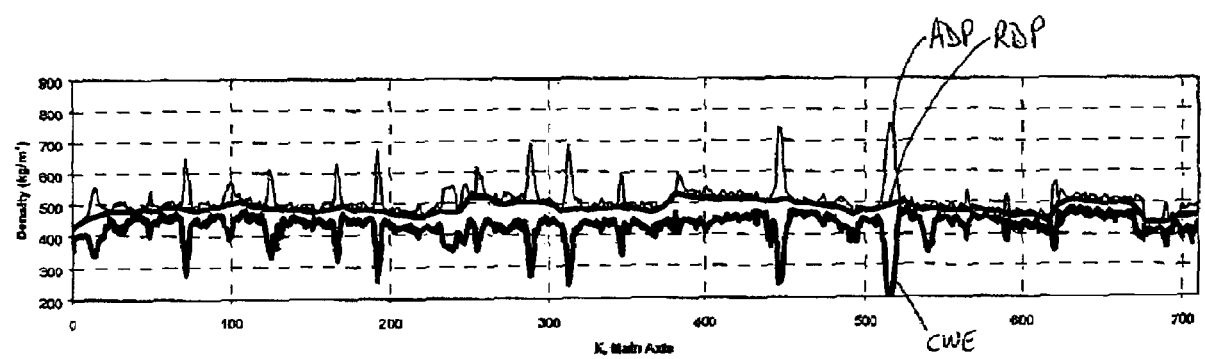
FIG. 1D shows an example of a density and clear wood equivalent profile for a virtual detector (pixels of the same index j) along the board main axis X. The upper-most graph (with peaks pointing upwards) show actual density profile with its reference density profile below. The density peaks correspond to knots. The lower-most profile (with peaks pointing downwards) shows clear wood equivalent density.
Figure 1E:
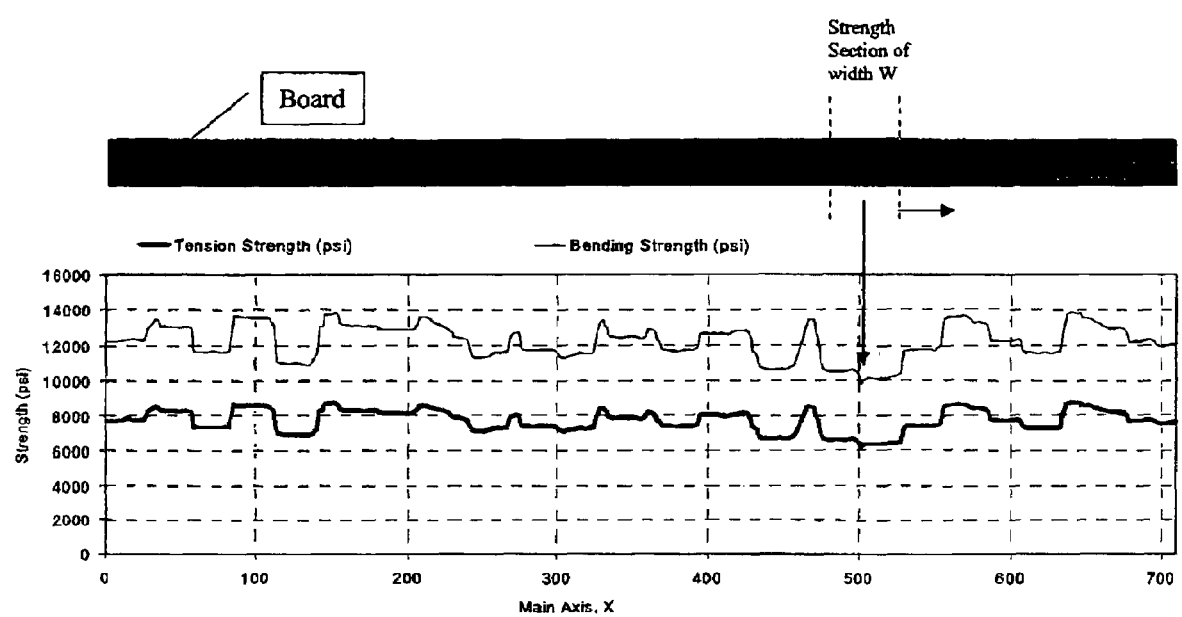
FIG. 1E shows an example of predicted tension and bending profiles along the board main axis X, showing the lowest point (minimum) computed from a moving section along the board main axis.
Figure 1F:
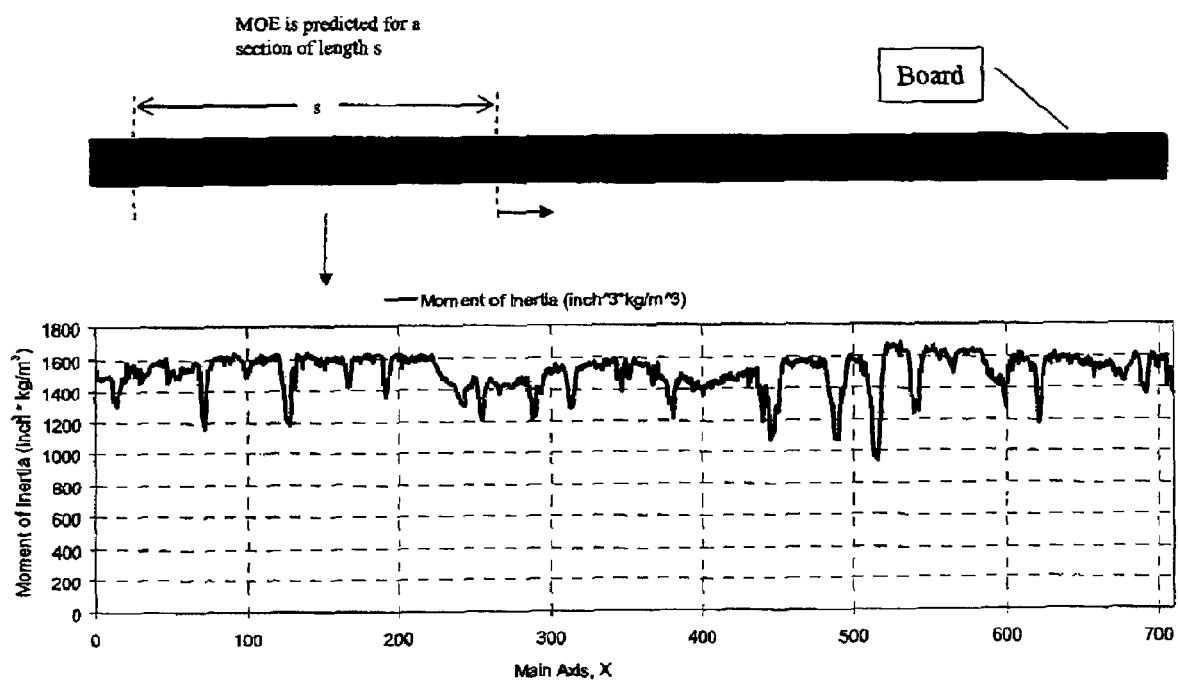
FIG. 1F shows an example of moment of inertia profile with a section of a board used to compute modulus of elasticity (MOE) for a given location where prediction of modulus of elasticity (MOE) is computed using moment of inertia within a section of length s that moves along the board main axis.
Figure 1G:
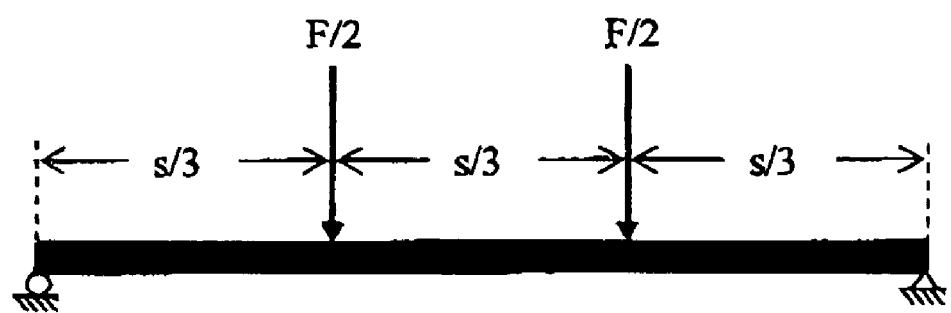
FIG. 1G illustrates loading conditions assumed for computation of predicted modulus of elasticity (MOE) using moment of inertia within a section of length s.

On the other hand, for a uniform beam with loading conditions as in FIG. 1g, the solution for E is $$E = \frac{23Fs^3}{1296IV_{max}} \tag{24j}$$

or for the same cross-section and span (24j) simplifies to $$E = D\frac{F}{V_{max}} \quad (24k)$$

Where D is a constant representing a size of a board cross-section.
Therefore a quantity to estimate is $$\frac{F}{V_{max}}$$

only.

This, compared with the solution (24h), yields final MOE estimation $E_{est}$ $$E_{Est} = D\frac{1}{K}$$

Strength Prediction

Strength is predicted lengthwise for a section (window) along nominal main board axis X (nominal grain direction). Therefore a particular predicted strength is assigned to a center of a window lengthwise, as shown in FIG. 1E. These sections may overlap resulting with a complete strength profile for a wood product, such as lumber. Window length correspond to approximate size of typical wood fracture and generally increases with lumber width size (greater width size, greater the window). The final strength value assigned to a tested product is minimum strength within the strength profile.

Strength is computed on the basis of a running window along wood main axis (length), as illustrated in FIG. 1C, involving following steps:

a) get minimum CWE within a longitudinal slice, $e_j^{MIN}$ where the slice consists of virtual pixels in the same width position $$e_j^{MIN} = \text{Min}_{i=0}^{i=W-1}(e_{ij}) \quad (25)$$

Where i is pixel index within window, i=0 ... W−1
and W is window size in virtual lines b) compute overall CWE density for the window as a weighted sum $$e = \sum_{j=1}^{K} w_j \cdot e_j^{MIN} \quad (26)$$

Where $w_j$ is cross-sectional weight, greater at wood edges and less in the middle. The weight function is different for UTS and MOR and in general subject to model optimization.

c) computes strength from CWE density tension strength (UTS) relationship $$UTS = f^{UTS}(e) \quad (27)$$

And bending strength (MOR)

$$MOR = f^{MOR}(e) \quad (28)$$

where $f^{UTS}$ and $f^{MOR}$ are optimized relationships between CWE and UTS and MOR.

The density to tension and bending strength functions are based on experimental data conducted on clear wood specimens and/or are in general the subject of model optimization.

In particular, the following model may be used $$UTS = Ae^p = f^{UTS}(e) \quad (29)$$

and $$UTS = Be^r = f^{UTS}(e) \quad (30)$$

where A, p, B, r are empirical (optimized) constants.

d) Final wood strength is a minimum of all windows strength values

MC Modeling Based on Microwave and X-Ray Density Measurement

Moisture content is predicted based on microwave and/or X-ray density, for:

(a) Microwave amplitude, and in particular: amplitude when microwave is polarized in transverse direction, amplitude when microwave is polarized in longitudinal direction, in form $$mc = Ka^n, \quad (31)$$

where K and n are empirical constants, and a is microwave amplitude.

(b) Microwave amplitude and X-ray density, and in particular, amplitude when microwave is polarized in transverse direction and X-ray density, amplitude when microwave is polarized in longitudinal direction and X-ray density, in form:

$$mc = Ka^n d^n \quad (32)$$

where K, m, and n are empirical constants, a is microwave amplitude, and d is X-ray density.

Model Optimization

Most models described here require optimization of the parameters (constants). Initial values for these parameters are taken from literature, using known relationships or from empirical data. Fine-tuning of these values for a specific species/size involves parameter optimization for maximum correlation with actual strength or stiffness, minimum prediction error, etc.

Any method for multidimensional function optimization may be used, including genetic algorithms, random walk, and similar techniques, Powell's methods, and Gradient methods.

Models may be optimized for:
a) All sizes and species,
b) Same sizes of the same species or species group, and
c) Particular size and species.

Stiffness Estimation from Machine Induced Wood Vibration

Vibration of a wood piece as it passes through a grading machine 10 is used to estimate stiffness (MOE). Vibration profile may be collected with a laser/camera scanner, here referred to as a 3D sensor. Vibration is induced by machine feeding mechanics.

Machine Geometry and Wood Dynamics

As wood behavior is linked with machine geometry and its position, the 3D-profile is segmented into different sections limited with characteristic points.

Figure 4:
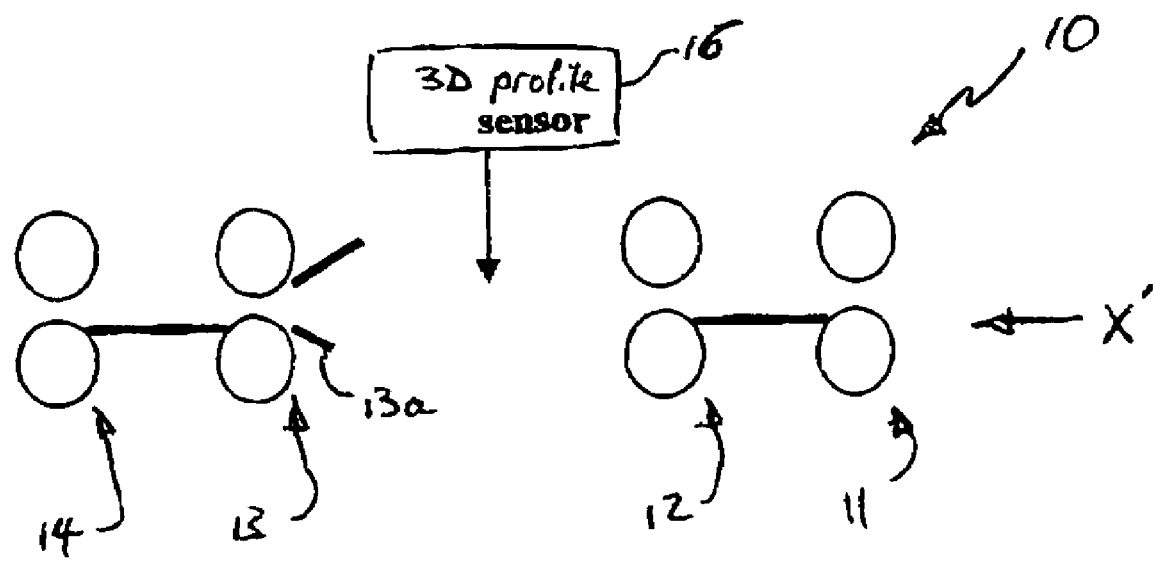
FIG. 4 illustrates a linear grading machine geometry, showing infeed wheel sets #1 and #2, outfeed wheel sets #1 and #2, and 3D-profile sensor.
Figure 5:
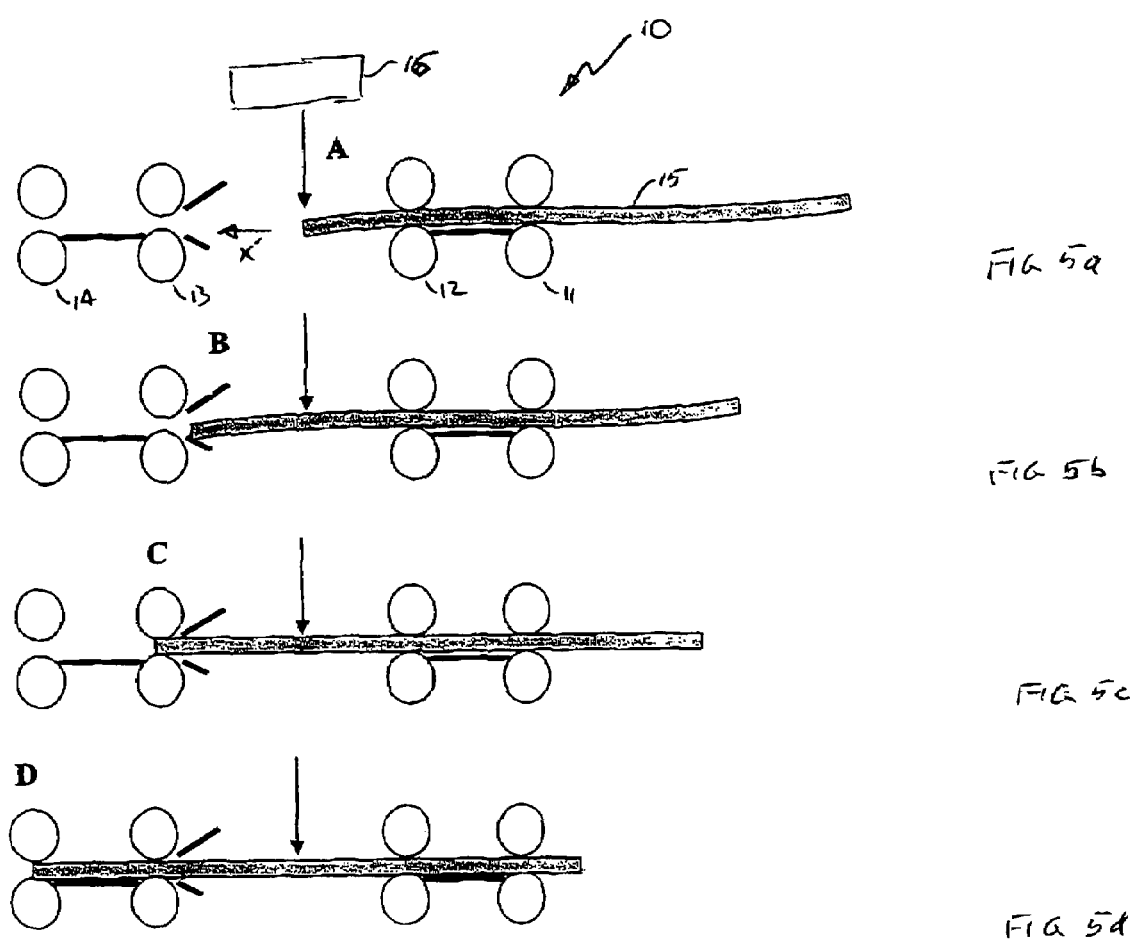
Figure 6:
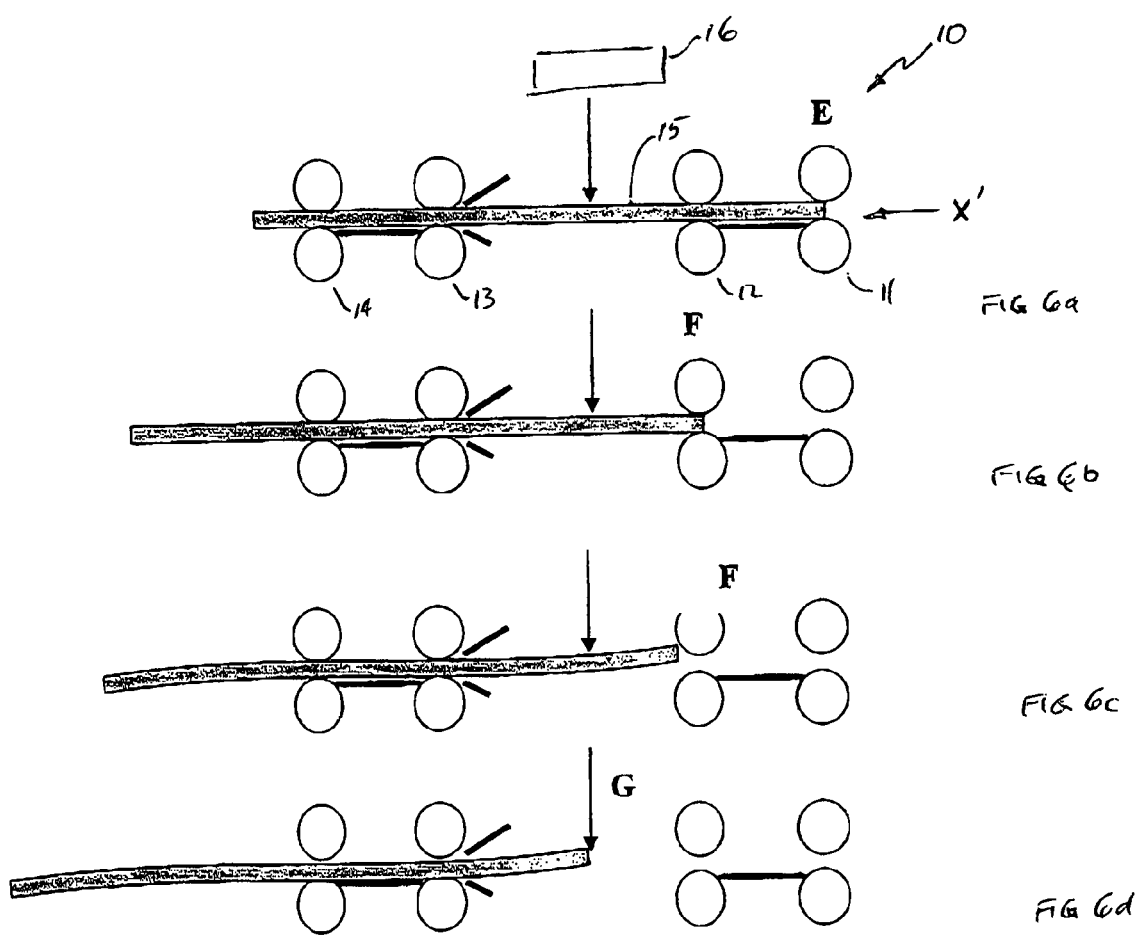
FIG. 6 is continued board behavior as it passes through the linear grading machine having characteristic points E, F, and G and a board adjustment before and after the characteristic point F, wherein:
- a) in FIG. 6A the board trailing end is at point E
- b) in FIG. 6B the board trailing end is at point F
- c) in FIG. 6C the board trailing end has passed point F
- d) in FIG. 6D the board trailing end is at point G.

A simplified grading machine geometry is show in FIG. 4. Wheel sets 11, 12, 13, and 14 follow the direction of the lumber flow X'.

Wood piece 15 enters the machine from right to left, passing through wheel sets 11 and 12 and into the field of view of 3D 15 sensor as shown in FIGS. 4 and 5A-D. First collected profile point is at characteristic point A in the field of view of sensor 15. From point A until the wood meets in feed guide 13a (characteristic point B), the leading end of the wood piece is fully unconstrained or free. This defines a first 3D profile section, AB. Following on downstream in direction X' as seen in FIGS. 6a-6d, more characteristic points are defined as follows, where, at point:

C the leading end of wood 15 meets wheel set 13
D the leading end of wood 15 meets wheel set 14
E the trailing end of wood 15 leaves wheel set 11
F the trailing end of wood 15 leaves wheel set 12
G the trailing end of wood 15 leaves 3D sensor 16
and sections,
AC unconstrained
CD semi-constrained
DE fully-constrained
EF semi-constrained
FG unconstrained.

From FIGS. 5a-5d and 6a-6d, it may be noted that only sections AB (or AC) and FG is statically undistorted by the machine. Because of unconstrained conditions, a free vibration takes place in these sections.

For the "S-shaped" wood in FIGS. 6A-D, one could expect a wood behavior, resulting with the following 3D profile:

a. In section AC (or AB) unconstrained, Z is less than the reference (base) line X", and free vibrations with large amplitude take place. The frequency of vibration decreases because of increasing span.

b. As the wood passed through characteristic point B or C, it is adjusted up, resulting with Z values greater than reference in semi-constrained section CD. Vibration amplitude in this section is somewhat reduced and higher in frequency than in section AB.

c. In fully-constrained section DE, wood behavior is somewhat undefined. However because of the constrained condition, reduced amplitude and increased frequency is expected.

3D Profile Sections

Figure 7:
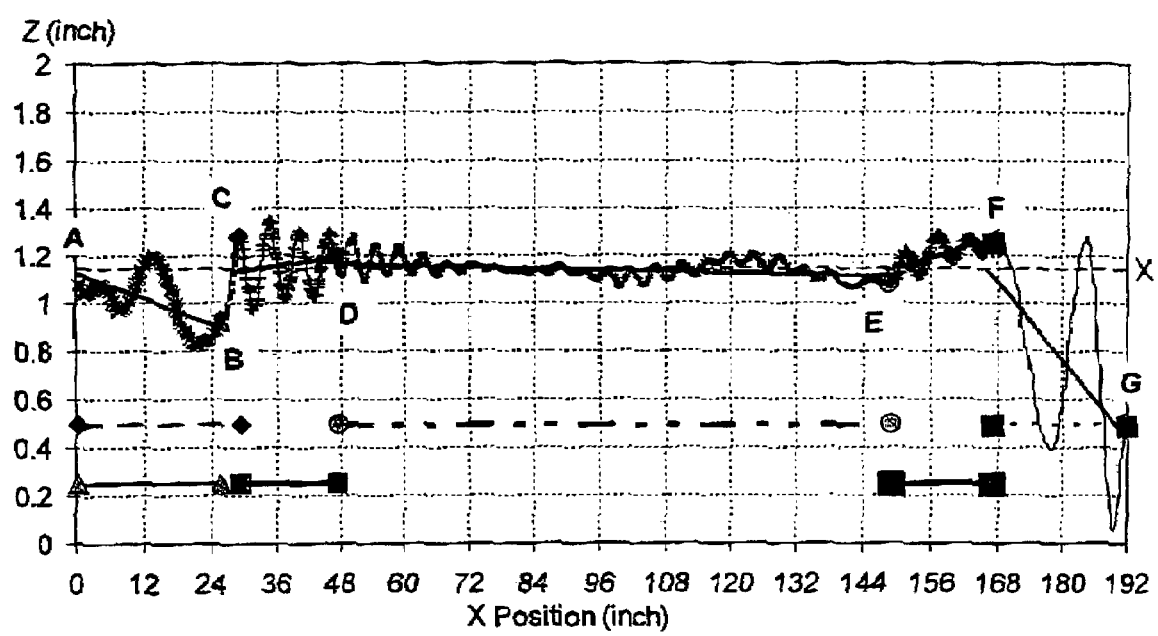
FIG. 7 is 3D-profile sensor profile segmented into different sections using characteristic points of FIGS. 5A-D and 6A-D.

The scenario of wood behavior and a resulting 3D profile is put to the test by segmenting the profile into sections using characteristic points and comparing the expectations with the actual wood shape. FIG. 7 shows the 3D profile of FIGS. 5A-D and 6A-D with characteristic points and trend lines for every section. The characteristic points were defined based on machine geometry. For example, the distance between point A and C correspond to the distance between 3D sensor 16 and center of the wheel set 13. Points A, B, C, and D were measured in reference to the start of 3D-profile sensor profile whereas points G, F, and E were measured in reference to the end of the 3D-profile.

Visual examination of the segmented profile in FIG. 7 confirms presence of distinct sections in the signal. Expected frequency and amplitude of unconstrained sections AB and FG, adjustments as points B, (or C), and F, and relatively leveled fully constrained section DE are confirmed.

Free Vibration of the Wood

Assuming a uniform cantilevered beam model, the lowest mode of vibration will have frequency $$f = 2\text{Pi}(1.875)^2 (EI/ma^4)^{1/2} \quad (38)$$

Where
Pi=3.14
E is elastic modulus
a is the span
I wood cross-sectional moment of inertia
m is distributed mass.

Frequency therefore is strongly affected by the span, as $f$ is proportional to $1/a^2$. Because span changes as the wood passes through the machine, the vibration frequency decreases in the start section (AB) and increases in end section (FG). This explains 3D signals at the wood start and the end shown in FIGS. 5A-D. This equation may be used for stiffness extraction.

Frequency for the semi-constrained and full-constrained conditions will have a more complex solution. However, the general relationship to E, I, and m, is similar, and sufficient to construct E (MOE) prediction model in general form.

$$E = Kf^2 m/I \quad (39)$$

where K is a constant than contains effect of type of constraint as well as span a effect. I is constant for a particular lumber size and m could be also assumed constant or measured, with X-ray for example.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A method of non-destructive testing of a wood piece using a multiplicity of sensors comprising the steps of:
   sensing the wood piece;
   collecting information from the sensors; and
   integrating the information into a model on a computer providing for strength and stiffness prediction;
   wherein collecting information includes collecting information relating to material characteristics of the wood piece and information relating to fiber quality characteristics of the wood piece;
   wherein the information relating to material characteristics includes at least two of a growth ring thickness, grain angle deviation, clear wood density, knot location, knot density, knot type, knot size, or location in the tree from which the wood piece was cut; and
   wherein the information relating to fiber quality characteristics includes at least one of a microfibril angle, juvenile wood, biodeterioration, manufacturing or drying defects, or reaction wood species
   wherein the model is constructed by:
      measuring material density in a plurality of dimensions on the wood piece;
      estimating other wood volume characteristics, including grain angle, growth ring angle, location in the tree from which the wood piece was cut, fiber quality including microfibril angle, and 3D geometry of the scanned piece;
      reducing clear wood equivalent density by effect of the wood volume characteristics using relationships of these characteristics on mechanical behavior of wood;
      further reducing clear wood equivalent density by effect of wood defects in respective locations of occurrence and effect of wood defects on mechanical behavior of wood; and
      constructing strength and stiffness models using clear wood density equivalent.

2. The method of claim 1 wherein sensing the wood piece is performed by at least one or more sensor types: X-ray, microwave, camera vision, laser triangulation three-dimensional geometry, material vibration measurements, or laser based tracheid effect measurement.

3. The method of claim 1 wherein the model is a physical model.

4. A method of predicting strength and stiffness of a wood piece using a multiplicity of sensor information gathered about the wood piece, the method comprising the following steps:

measuring the piece with a multiplicity of sensors to obtain measured information;

estimating wood volume characteristics to obtain estimated information, the wood volume characteristics including one or more of the following: clear wood density, grain angle, moisture content, growth ring angle, location in the tree from which the wood was cut, fiber quality including mirofibril angle, and three dimensional geometry;

detecting size, location, and classification of wood defects to obtain detected information, the wood defects including one or more of the following: knots, biodeterioration, reaction wood, juvenile wood, manufacturing and drying defects, pith, pitch, wet pockets;

inputting measured, estimated or detected information into a physical model of the wood piece, the physical model being located on a computer; and predicting strength and stiffness based on effect of estimated information and detected information on mechanical behavior of the wood piece;

wherein predicting strength and stiffness comprises:

measuring material density in a plurality of dimensions on the wood piece;

estimating other wood volume characteristics, including grain angle, growth ring angle, location in the tree from which the wood piece was cut, fiber quality including microfibril angle, and 3D geometry of the scanned piece;

reducing clear wood equivalent density by effect of the wood volume characteristics using relationships of these characteristics on mechanical behavior of wood;

further reducing clear wood equivalent density by effect of wood defects in respective locations of occurrence and effect of wood defects on mechanical behavior of wood; and constructing strength and stiffness models using clear wood density equivalent;

wherein the step of predicting strength and stiffness includes the step of estimating effect of the grain angle by decomposing the grain angle into running average and local deviation components, wherein said running average component is a function ($g_{ave}$ (GA)) of running average grain angle along a length of the wood piece excluding grain deviations around knots, and wherein said local deviation component is a function ($g_{dev}$ (GA)) of said grain angle defined as a difference between a local measured grain angle and said running average grain angle, and further includes the step of computing grain angle effect functions $g_{ave}$ (GA) and $g_{dev}$ (GA) for determining the effect of grain angle on a material property wherein both $g_{ave}$ (GA) and $g_{dev}$ (GA) are computed according to the following equation:

$$g(GA) = \frac{1}{R \cdot \sin^n(GA) + \cos^m(GA)}$$

wherein n, m, are empirical constants, R is the ratio between the material property measured parallel to the grain versus the material property measured perpendicular to the grain, and optimizing constants R, n, and m are specific to the species corresponding to the wood piece, applying said running average modification function ($g_{avg}$ (GA)) to the clear wood equivalent density by multiplication according to:

$$e'_{ij} = e_{ij} * g_{avg}(GA_{ij})$$

modifying the grain deviation function ($g_{dev}$(GA)) to derive a further grain angle deviation modification function to avoid multiple density reduction due to knot detected in density according to:

$$g'_{dev}(GA_{ij}, k_{ij}) = g_{dev}(GA_{ij}) + (1 - g_{dev}(GA_{ij}))k_{ij}/T$$

wherein T is a constant threshold value density, and applying said grain angle deviation modification function $g'_{dev}(GA_{ij}, K_{ij})$ to clear wood equivalent density by multiplication $$e'_{ij} = e_{ij} * g'_{dev}(GA_{ij}, k_{ij}).$$

5. The method of claim 4 wherein measuring material density is performed by X-ray, microwave, camera vision, laser triangulation three-dimensional geometry, material vibration measurements, or laser-based tracheid effect measurement.

6. The method of claim 4, further comprising estimating clear wood equivalent in an area of the wood piece occupied by a knot by virtually removing density occupied by a knot and replacing it by a density of clear wood, mechanically equivalent to the removed knot.

7. The method of claim 6, wherein said sensors include a sensor collecting pixel values from a corresponding matrix of pixels in said sensor, and wherein for every pixel density, $d_{ij}$, said method includes the step of computing clear wood equivalent, $e_{ij}$, using adaptive threshold clear wood density, $a_{ij}$, in the equation:

$$e_{ij} = \text{RemaingClearWood} + \text{KnotEquivalent}$$

wherein:

$$\text{RemaingClearWood} = a_{ij} - k_{ij} * K$$

i is virtual pixel index along the length of the wood piece j is virtual pixel index traversely across the wood piece K is knot density ratio, defined as a ratio of clear wood density to density of knot knot density is difference between wood density $d_{ij}$ and clear wood density $$k_{ij} = d_{ij} - a_{ij}$$

KnotEquivalent is defined as clear wood density equivalent residing in knot volume, $$\text{KnotEquivalent} = k_{ij} * K * M$$

wherein M is the material knot property ratio:

$$M = \text{Knot Property/Clear Wood Property}.$$

8. The method of claim 7 wherein the step of computing $e_{ij}$ includes substituting:

$$e_{ij} = a_{ij} + (d_{ij} - a_{ij}) * K * (M - 1).$$

9. A method of non-destructive testing of a wood piece using a multiplicity of sensors comprising the steps of:

sensing the wood piece;

collecting information from the sensors; and integrating the information into a model on a computer providing for strength and stiffness prediction;

wherein collecting information includes collecting information relating to material characteristics of the wood piece and information relating to fiber quality characteristics of the wood piece;
wherein the information relating to material characteristics includes at least two of a growth ring thickness, grain angle deviation, clear wood density, knot location, knot density, knot type, knot size, or location in the tree from which the wood piece was cut; and
wherein the information relating to fiber quality characteristics includes at least one of a microfibril angle, juvenile wood, biodeterioration, manufacturing or drying defects, or reaction wood species
wherein the model is constructed by:
    measuring material grain angle in a plurality of dimensions on the wood piece;
    constructing clear wood zero grain angle equivalent by assigning a nominal density value which is an average for a wood species whenever grain angle relative to a longitudinal axis of the wood piece is zero, and less wherever the grain angle deviates from and accordingly to grain angle effect on mechanical behavior of wood;
    reducing clear wood equivalent density by effect of the wood volume characteristics using relationships of these characteristics on mechanical behavior of wood;
    further reducing clear wood equivalent density by effect of wood defects in respective locations of occurrence and effect of wood defects on mechanical behavior of wood; and
    constructing strength and stiffness models using clear wood density equivalent.

10. The method of claim 9 wherein sensing the wood piece is performed by at least one or more sensor types: X-ray, microwave, camera vision, laser triangulation three-dimensional geometry, material vibration measurements, or laser based tracheid effect measurement.

11. The method of claim 9 wherein the model is a physical model.

12. The method of claim 9 wherein said sensors include a sensor collecting pixel values from a corresponding matrix of pixels in said sensor, and wherein for every pixel density, $d_{ij}$, said method includes the step of computing clear wood equivalent, $e_{ij}$, using adaptive threshold clear wood density, $a_{ij}$, in the equation:

$$e_{ij} = \text{RemaingClearwood} + \text{KnotEquivalent}$$

wherein:

$$\text{RemaingClearWood} = a_{ij} - k_{ij}*K$$

i is virtual pixel index along the length of the wood piece
j is virtual pixel index traversely across the wood piece
K is knot density ratio, defined as a ratio of clear wood density to density at knot knot density is difference between wood density $d_{ij}$ and clear wood density $$k_{ij} = d_{ij} - a_{ij}$$

KnotEquivalent is defined as clear wood density equivalent residing in knot volume, $$\text{KnotEquivalent} = k_{ij}*K*M$$

wherein M is the material knot property ratio:

$$M = \text{Knot Property}/\text{Clear Wood Property}.$$

13. The method of claim 12 wherein the step of computing $e_{ij}$ includes substituting:

$$e_{ij} = a_{ij} + (d_{ij} - a_{ij})*K*(M-1).$$

14. The method of claim 9 wherein the step of predicting strength and stiffness includes the step of estimating effect of the grain angle by decomposing the grain angle into running average and local deviation components, wherein said running average component is a function ($g_{ave}$ (GA)) of running average grain angle along a length of the wood piece excluding grain deviations around knots, and wherein said local deviation component is a function ($g_{dev}$ (GA)) of said grain angle defined as a difference between a local measured grain angle and said running average grain angle, and further includes the step of computing grain angle effect functions $g_{ave}$ (GA) and $g_{dev}$ (GA) for determining the effect of grain angle on a material property wherein both $g_{ave}$ (GA) and $g_{dev}$ (GA) are computed according to the following equation:

$$g(GA) = \frac{1}{R \cdot \sin^n(GA) + \cos^m(GA)}$$

wherein n, m, are empirical constants, R is the ratio between the material property measured parallel to the grain versus the material property measured perpendicular to the grain, and optimizing constants R, n, and m are specific to the species corresponding to the wood piece,
    applying said running average modification function ($g_{avg}$ (GA)) to the clear wood equivalent density by multiplication according to:

$$e'_{ij} = e_{ij}*g_{avg}(GA_{ij})$$

modifying the grain deviation function ($g_{dev}$(GA)) to derive a further grain angle deviation modification function to avoid multiple density reduction due to knot detected in density according to:

$$g'_{dev}(GA_{ij}, k_{ij}) = g_{dev}(GA_{ij}) + (1 - g_{dev}(GA_{ij}))k_{ij}/T$$

wherein T is a constant threshold value density, and
    applying said grain angle deviation modification function $g'_{dev}(GA_{ij}, K_{ij})$ to clear wood equivalent density by multiplication $$e'_{ij} = e_{ij}*g'_{dev}(GA_{ij}, k_{ij}).$$

* * * * *

UNITED STATES PATENT AND TRADEMARK OFFICE
CERTIFICATE OF CORRECTION

PATENT NO. : 7,680,304 B2
APPLICATION NO. : 10/854930
DATED : March 16, 2010
INVENTOR(S) : Jacek M. Biernacki et al.

It is certified that error appears in the above-identified patent and that said Letters Patent is hereby corrected as shown below:

Column 20, Lines 40 through 45, should have ";" at the end of the lines, beginning with the equation on Line 40.

The equation in Column 20, Line 49 should end with a ";" followed by "and,".

The equation in Column 21, Line 50 should end with a ";".

Column 21, Lines 51 and 52 (currently ending with "piece") should end with a ";".

Column 21, Line 54 should end with the words "density to density of knot;".

Column 21, Lines 55 and 56 should read: "knot density is difference between wood density $d_{ij}$ and clear wood density" – the following equation should be on its own line, ending with a ";" and the word and.

Column 22, Line 1: There should be a space between "KnotEquivalent" and "is".

Column 22, Line 49: The final section of the equation should read: $(GA_{ij}))k_{ij}/T$ – one parenthesis is missing before the letter k.

Signed and Sealed this

Fourth Day of May, 2010

David J. Kappos
*Director of the United States Patent and Trademark Office*